United States Patent
Olsson et al.

(10) Patent No.: US 6,527,719 B1
(45) Date of Patent: Mar. 4, 2003

(54) ULTRASONIC DIAGNOSTIC IMAGING SYSTEM WITH REDUCED POWER CONSUMPTION AND HEAT GENERATION

(75) Inventors: Lars Jonas Olsson, Woodinville, WA (US); Paul Wittrock, Carnation, WA (US); Andrew L. Robinson, Kirkland, WA (US); Kenneth R. Linkhart, Seattle, WA (US); Boyd Edmondson, Bothell, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 205 days.

(21) Appl. No.: 09/695,644

(22) Filed: Oct. 24, 2000

Related U.S. Application Data
(60) Provisional application No. 60/232,450, filed on Sep. 13, 2000.

(51) Int. Cl.[7] .................................................. A61B 8/00
(52) U.S. Cl. .................... 600/443; 600/437; 73/321; 73/324; 395/750
(58) Field of Search .......................... 600/443, 437; 713/321, 324; 395/750

(56) References Cited

U.S. PATENT DOCUMENTS

| | | | |
|---|---|---|---|
| 5,083,266 A | * | 1/1992 | Watanabe ............... 713/321 |
| 5,142,684 A | | 8/1992 | Perry et al. |
| 5,396,443 A | | 3/1995 | Mese et al. |
| 5,456,256 A | | 10/1995 | Schneider et al. |
| 5,487,386 A | | 1/1996 | Wakabayashi et al. |
| 5,504,907 A | * | 4/1996 | Stewart et al. ........... 713/321 |
| 5,511,205 A | * | 4/1996 | Kannan et al. ........... 713/324 |
| 5,654,509 A | | 8/1997 | Miele et al. |
| 5,675,808 A | | 10/1997 | Gulick et al. |
| 5,822,034 A | | 10/1998 | Shimashita et al. |
| 5,851,186 A | | 12/1998 | Wood et al. |
| 5,897,498 A | | 4/1999 | Canfield, II et al. |
| 5,924,979 A | | 7/1999 | Swedlow et al. |
| 5,938,607 A | | 8/1999 | Jago et al. |
| 5,964,708 A | | 10/1999 | Freeman et al. |
| 5,997,479 A | | 12/1999 | Savord et al. |
| 6,013,032 A | | 1/2000 | Savord |
| 6,083,168 A | | 7/2000 | Hossack et al. |
| 6,251,073 B1 | * | 6/2001 | Imran et al. ............. 600/443 |

OTHER PUBLICATIONS

"Advanced Configuration and Power Interface Specification," Intel, Microsoft, Toshiba, pp 1–51, 219–228, Revision 1.0b, Feb. 2, 1999.
"Chapter 10—Mobile Computing," Technical Information—Apr. 2000, pp 1–32, Microsoft Corporation.
"OnNow: The Evolution of the PC Platform," microsoft.com Guide—Jun. 9, 2000, pp 1–13, http://www.microsoft.com/hwdev/desinit/ONNOW1.htm.
"Chapter 20—Power Management," Technical Information—Apr. 2000, pp 1–14, Microsoft Corporation.

\* cited by examiner

Primary Examiner—Marvin M. Lateef
Assistant Examiner—Ruby Jain
(74) Attorney, Agent, or Firm—W. Brinton Yorks, Jr.

(57) ABSTRACT

An ultrasound system is described which exhibits reduced power consumption and improved reliability. When the ultrasound system is idle for a period of time it automatically invokes a sequence of energy-saving procedures, including readying the system for use at a predetermined time. The use of periodically invoked low power states, even if only for seconds at a time, will over the long term save energy including the cost of air conditioning the site of the ultrasound system. Such low power states also reduce the heat dissipation and exposure of components to heat, one of the major causes of component failure. Thus an embodiment of the present invention can improve ultrasound system reliability and long term effectiveness and cost.

3 Claims, 13 Drawing Sheets

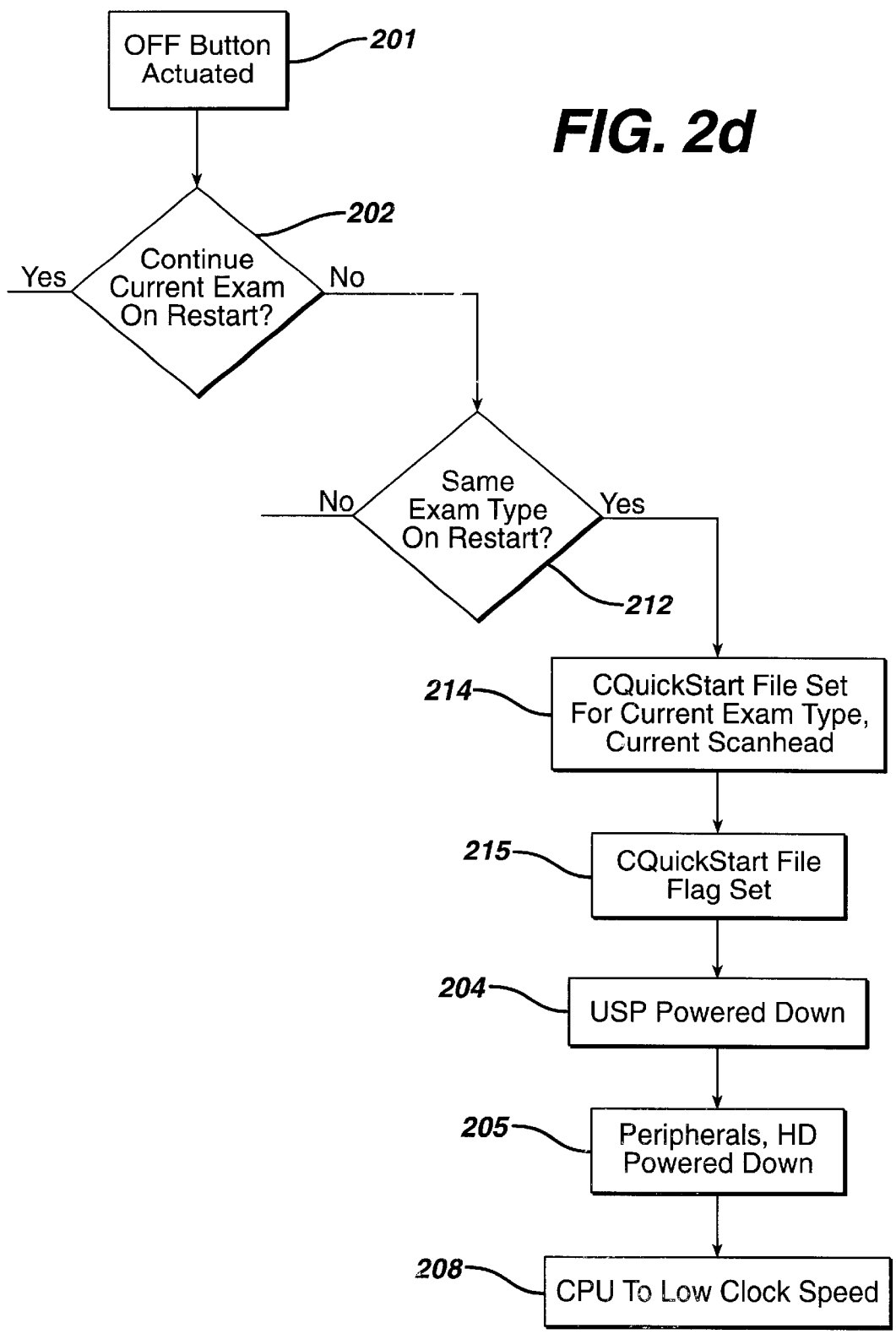

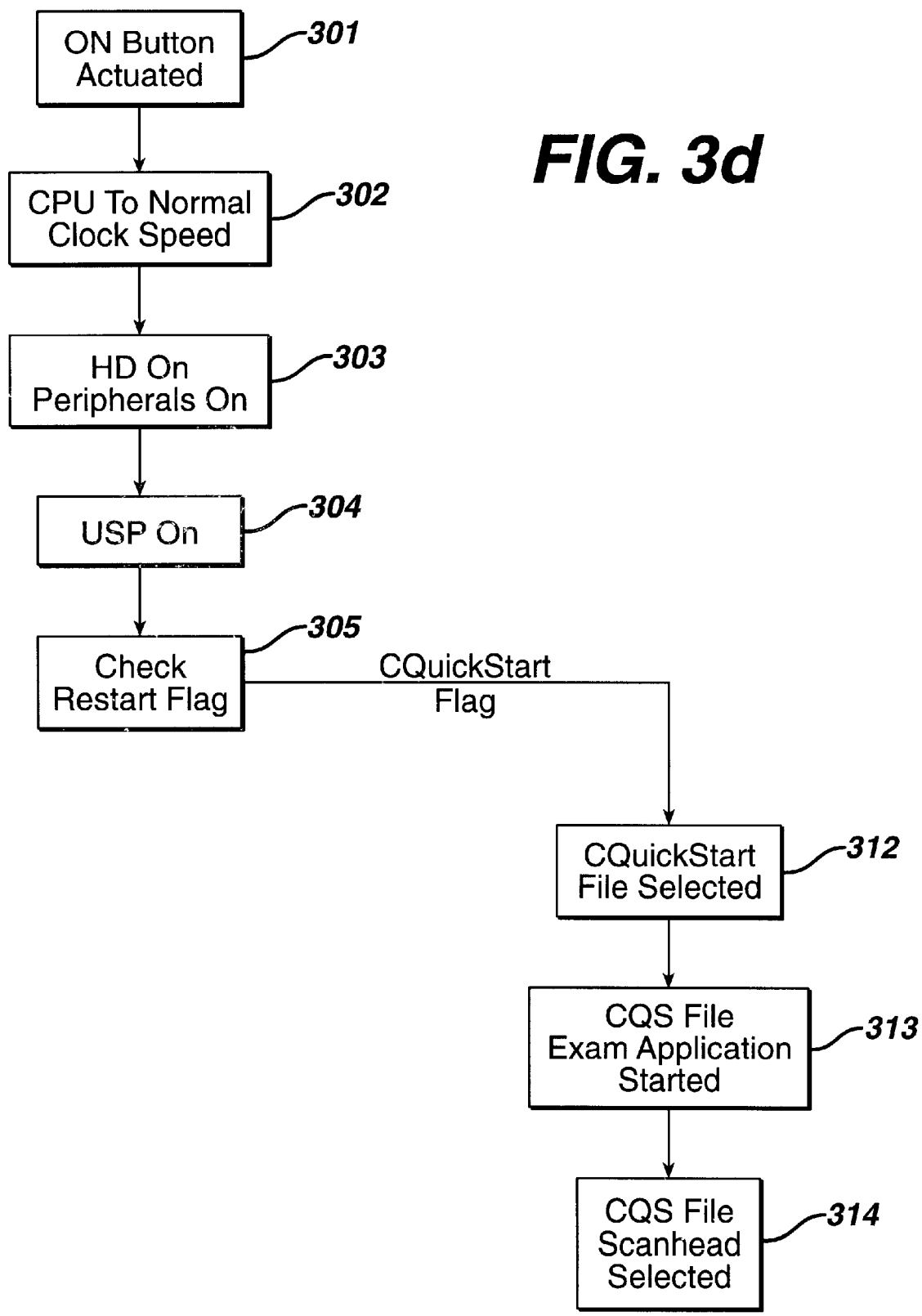

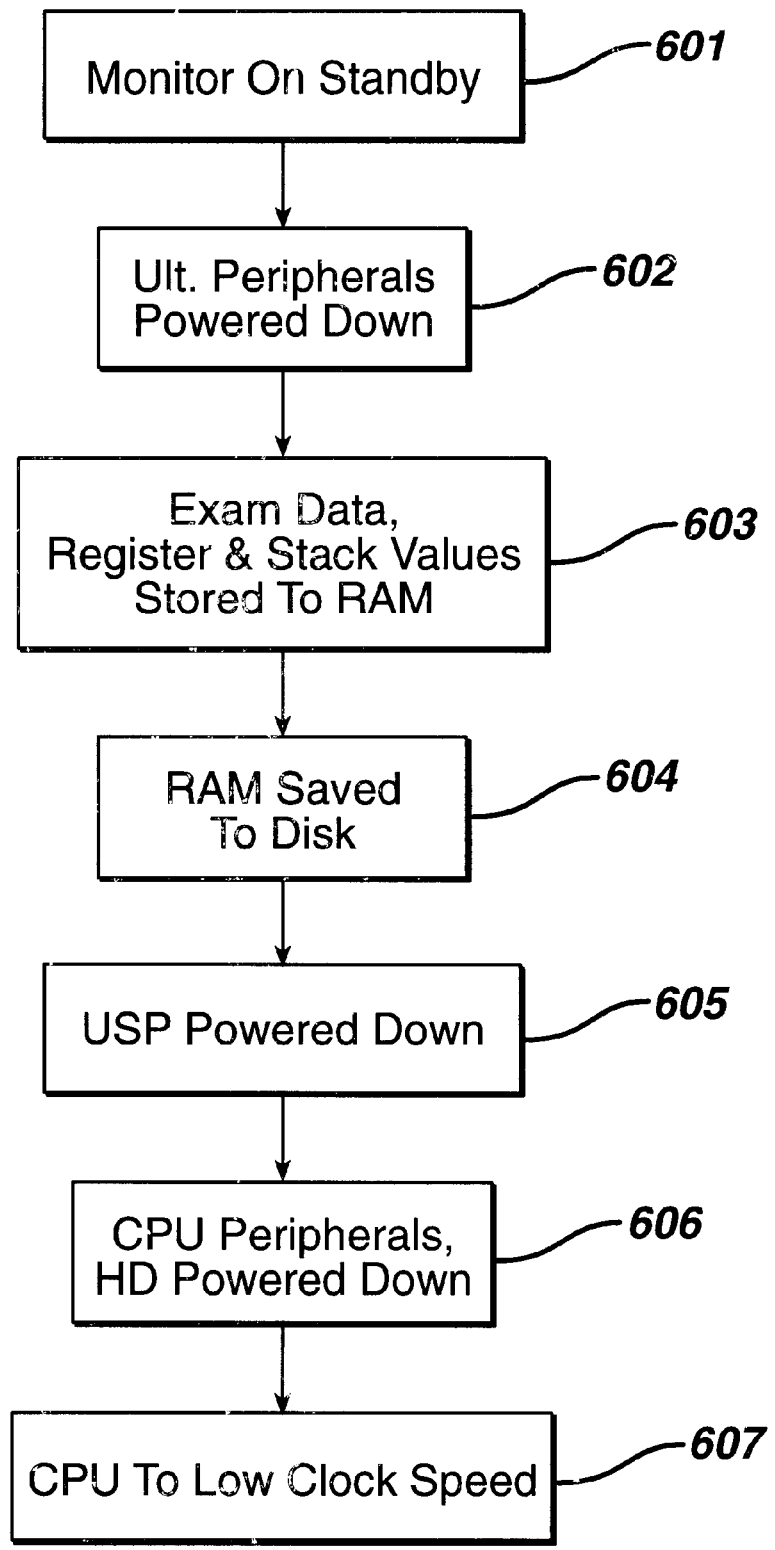

ULTRASONIC DIAGNOSTIC IMAGING SYSTEM WITH REDUCED POWER CONSUMPTION AND HEAT GENERATION

This application claims the benefit of Provisional U.S. patent application Ser. No. 60/232,450, filed Sep. 13, 2000.

This invention relates to ultrasonic diagnostic imaging systems and, in particular, to ultrasound systems with reduced power consumption and improved reliability.

Today's high performance ultrasound systems contain a substantial amount of sophisticated and custom circuitry which enable the systems to create high quality real-time images. This sophistication has led to the need for a complex and time-consuming boot-up procedure to initialize the system for diagnostic use each time it is turned on. The system user must wait for the boot-up procedure to conclude before the system can be used for scanning. Once the system is fully operational it can consume in excess of 1000 watts of energy on a continual basis. When it system is turned off, it proceeds through a lengthy sequence of steps to power down the system. Because of the aforementioned inconvenience and complexity of turning the ultrasound system off and on, ultrasound systems are frequently left on during periods of inactivity to avoid this delay. Sometimes an ultrasound system will be powered up continuously, and even left on overnight when it will not be used for many hours, simply as a matter of convenience. While the machine sits idle it continues to consume electricity and generate heat. It is thus desirable to minimize the power consumption of an ultrasound system during such periods of inactivity.

In accordance with the principles of the present invention, an ultrasonic diagnostic imaging system is described which can be turned off quickly and restarted and be ready for scanning in a matter of seconds. This is accomplished by allowing a processor and/or memory within the system to remain active even when the system is "turned off." When the system is turned off the state of the system is minimally preserved in either volatile or nonvolatile memory so that the system can restart without having to sequence through an entire bootup procedure. In a preferred embodiment the processor has a battery backup, enabling the processor to remain active even when the ultrasound system is unplugged and being moved. When the ultrasound system arrives at its destination, diagnosis can begin at once. When the ultrasound system is idle for a period of time it automatically invokes a sequence of energy-saving procedures, including readying the system for use at a predetermined time. The use of periodically invoked low power states, even if only for seconds at a time, will over the long term save energy including the cost of air conditioning the site of the ultrasound system. Such low power states also reduce the heat dissipation and exposure of components to heat, one of the major causes of component failure. Thus an embodiment of the present invention can improve ultrasound system reliability and long term effectiveness and cost.

In the drawings:

FIG. 1 illustrates in block diagram form an ultrasonic diagnostic imaging system constructed in accordance with the principles of the present invention;

FIG. 1*a* illustrates a method for initializing the ultrasound system of FIG. 1;

FIGS. 2*a*–2*d* illustrate different methods for efficiently turning off an ultrasound system so that it can be restarted quickly;

FIGS. 3*a*–3*d* illustrate different methods for rapidly restarting an ultrasound system;

FIG. 6 illustrates a method by which an ultrasound system assumes a state of lower power consumption during periods of inactivity.

Figure 1:
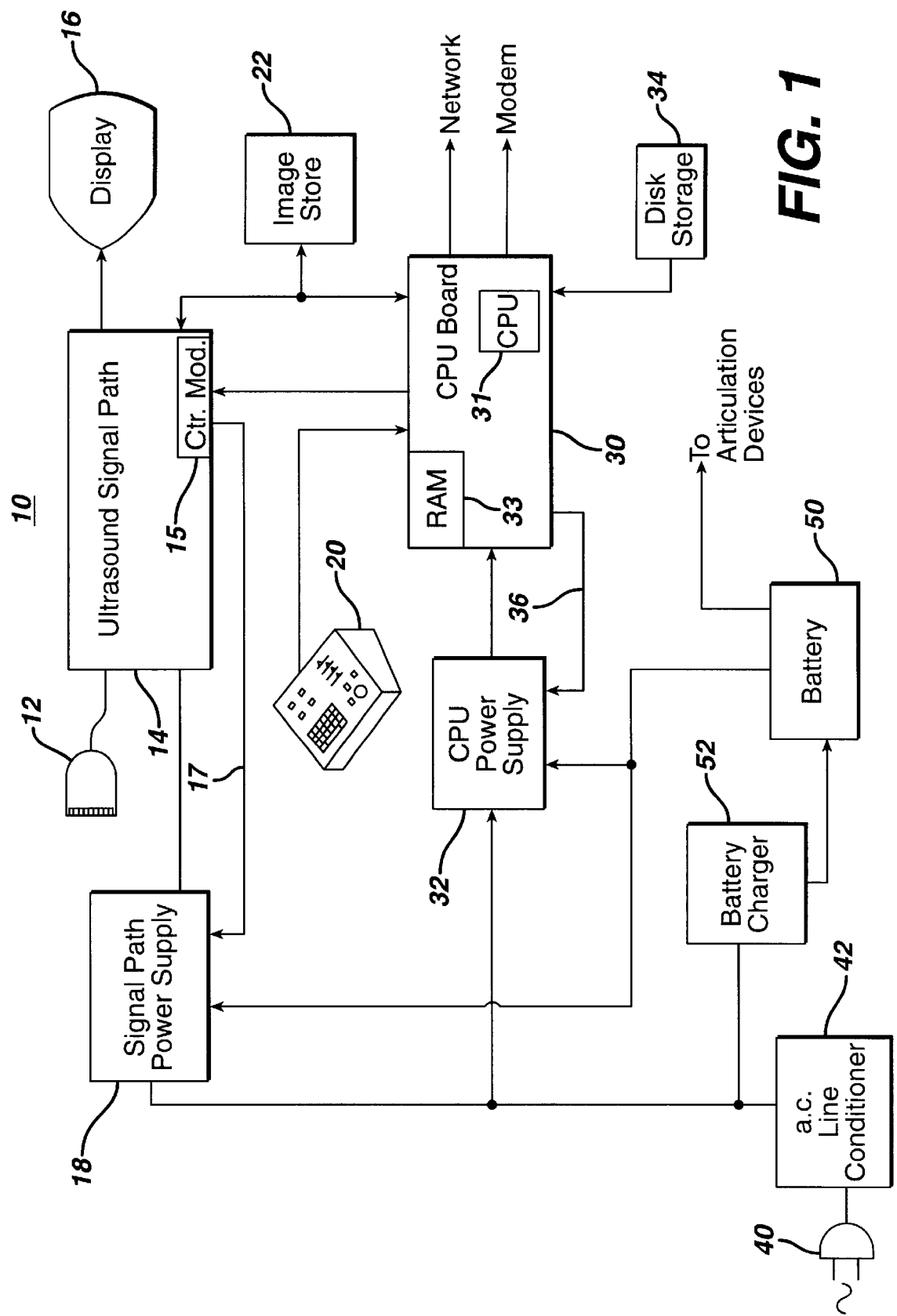

Referring first to FIG. 1, an ultrasonic diagnostic imaging system 10 constructed in accordance with the principles of the present invention is shown in block diagram form. The components of a typical ultrasound system are shown at the top of the drawing, including a scanhead or transducer 12, an image display 16, and the ultrasound signal path 14 which connects the transducer and the display. The ultrasound signal path will typically include a beamformer which controls the transmission of ultrasonic waves by the transducer 12 and forms received echo signals into steered and focused beams, a signal processor which processes coherent echo signals in the desired mode of display, e.g., B mode, Doppler mode, harmonic or fundamental mode, and an image processor which produces image signals of the desired format from the processed echo signals, such as a 2D or 3D image or spectral Doppler display. The ultrasound signal path is controlled in a coordinated manner by a system controller which responds to user commands and dictates the overall scheme of functionality of the ultrasound signal path. For instance, the system operator may enter a command on the user control panel 20 to request two dimensional colorflow imaging using a certain scanhead. The system controller would respond to this command by conditioning the beamformer to operate and control the desired scanhead, initializing the signal processor to Doppler process the received echo signals, and setting up the image processor to produce a grayscale B mode image with flow shown as a color overlay.

The source of energy for a cart-borne or tabletop ultrasound system is generally a.c. line voltage accessed by a plug 40. The a.c. power is filtered and rectified by an a.c. line conditioner 42, which produces a DC supply voltage such as 48 volts. This voltage is supplied to a signal path power supply 18, which supplies power to the scanhead 12 and ultrasound signal path 14. The a.c. line conditioner provides two other functions, which are to sense and respond to different a.c. power sources and to provide power factor correction which matches current and voltage phases to prevent instantaneous current spikes during cycles of the a.c. power. The a.c. line conditioner will sense whether the plug 40 is connected to 110 volt, 60 Hz power or 220 volt 50 Hz power, for instance, and will respond to configure the line conditioner to produce the required 48 VDC from either a.c. source. Power factor correction will cause the ultrasound system to use power more efficiently by appearing as a more resistive rather than reactive load to the a.c. power system. The power supply 18 is a DC to DC converter, which supplies a number of DC voltages for different components and modules of the ultrasound system. For instance, a high voltage is supplied as a drive voltage for the ultrasonic transducer, and lower level voltages are supplied to the digital processing circuitry of the system. The signal path power supply 18 is generally capable of providing 1000 watts or more of power to a cart-borne ultrasound system.

In accordance with the principles of the present invention a CPU board 30 is coupled to the ultrasound signal path 14 which controls the powering up and powering down of the ultrasound signal path. The functions of the CPU board discussed below may, in a particular embodiment, be integrated into the system controller of the ultrasound signal path and be performed there. In FIG. 1 a separate CPU board is shown for ease of illustration and understanding. The CPU board 30 may comprise an off-the-shelf motherboard such as an ATX form factor motherboard with a system core chipset and basic input/output (BIOS) software. BIOS is code that runs from some sort of non-volatile memory such as a PROM or flash storage device and stays resident on the CPU board. The BIOS software boots the CPU from a cold power-up and launches the operating system. The BIOS software performs such functions as checking basic hardware operability and hardware resources available. Vendors of BIOS software include Phoenix, Award, and American Megatrends. The CPU board includes a CPU processor 31 (sometimes referred to herein as the CPU) which may be a microprocessor such as the microprocessors available from Intel, Advanced Micro Devices, or Motorola, or a processor of more limited capability such as a reduced instruction set (RISC) processor. The CPU board includes a random access memory (RAM) 33 which enables the CPU to run an operating system software program (OS) resident on non-volatile disk storage 34. The OS is operated to control various operating aspects or the ultrasound signal path 14, display 16 and peripheral devices connected to the ultrasound system such as printers and recorders, as described below. The OS refers to the platform software that tends to housekeeping functions and provides an interface to launch application software. Operating system software includes DOS, Windows95-2000, Windows CE and NT, Solaris, and OS2. Any software that is not an OS and performs a given task is referred to as application software. Examples of application software includes word processor software, spreadsheet software, communication or analysis software, and the custom software that runs an ultrasound machine. In the illustrated embodiment the CPU board is coupled to the ultrasound signal path 14 by way of a control interface shown as control module 15 of the ultrasound signal path 14. When the functionality of the CPU board is integrated into the ultrasound signal path, the need for this interface may be partially or wholly eliminated.

The CPU board may be powered by the signal path power supply 18, however, in the illustrated embodiment the CPU board 30 is powered by its own CPU power supply 32. The CPU power supply has a lower capacity than that of the power supply 18, and may for instance be a 250 watt power supply. The CPU power supply 32, like the power supply 18, is a DC to DC converter which converts the voltage level supplied by the a.c. line conditioner to the DC voltages required by the CPU board 30 and, preferably, also the disk storage 34. The CPU power supply is coupled to the a.c. line conditioner and is energized in the same manner as the power supply 18.

In accordance with another aspect of the present invention, the ultrasound system includes an optional battery 50 which provides a backup source of power to the signal path power supply 18 and the CPU power supply 32. The battery is charged by a battery charger 52 coupled to the a.c. line conditioner 42 so that the battery can be fully charged whenever the plug 40 is connected to a source of a.c. line voltage. The battery 50 is also coupled to the drive motors of articulation devices, when present, by which movable parts of the ultrasound system such as the display 16 and control panel 20 can be raised, lowered, and tilted for the convenience of the operator. This enables the ultrasound system's articulated components to be moved and adjusted even when the system is not plugged into a wall outlet.

The ultrasound system has connections for a network and/or modem by which diagnostic information obtained by use of the ultrasound system can be remotely stored or shared with others. The network and modem connections also enable information from remote sources to be provided to the ultrasound system, such as electronic mail and reference image libraries as described in U.S. Pat. Nos. 5,897,498 and 5,938,607. In the embodiment shown in FIG. 1 these connections are made from the CPU board 30, although in a particular embodiment they may also be made from the ultrasound signal path 14.

When a conventional ultrasound system is turned on, it must initialize all of its functionality from a cold start, which can take many minutes to accomplish. Likewise, when the system is turned off, the ultrasound system goes through a lengthy process to power down its various modules and subsystems in an orderly but time consuming sequence. In an embodiment of the present invention, the CPU board is rarely, if ever, completely powered down. The CPU board controls the other components and subsystems of the ultrasound system to be in various suspended states or entirely powered down, and may even itself go into a suspend or low power state, but is selectively available to be restored and to restore the rest of the ultrasound system to full operation in a short or almost instantaneous period of time.

In concept, the CPU board 30 and its OS and associated software act as a central processor with the other elements of the ultrasound system, including the ultrasound signal path 14, in essence viewed as peripheral devices to this central processor. The CPU board OS and, if desired, application software control the states of operation of these peripheral devices, within the constraints dictated by the user, so that the entire system is run efficiently and effectively. This can entail directing other elements of the ultrasound system to be in a high state of readiness, or to be in various suspend states with different time periods to return to full operation and different levels of power consumption, or to be partially or completely powered down. Not only does the CPU board OS control other elements of the system in this way; in a preferred embodiment it can impose these same controls on itself, even to a state in which the entire system is in a suspend state where it is consuming only 5–10 watts or less of power and can thus be maintained by battery power for a substantial period of time.

Several examples will illustrate the degrees of control which are possible. If the OS detects a lengthy period of inactivity by the ultrasound system, it may progressively power down or suspend operation of certain system components. The display for instance, might first be set to standby, then later powered down completely. Similar action might be taken with peripheral devices such as printers and recorders. The periods of inactivity after which these actions are automatically performed can be set by the system operator. Selected elements and even major portions of the ultrasound system which take little or virtually no time to reactivate can be powered down even for short periods of time such as a few seconds. For instance, when the operator freezes an image on the display screen, major portions of the ultrasound signal path can be placed in a low power suspend state until realtime scanning is resumed. This suspend state would be unnoticed by the operator, to whom the system would always appear fully active. Such a suspend state might only last for a period of seconds, but the accumulation of such periods over time can result in a significant reduction in power consumption and component heat exposure and dissipation. Other elements of the system might always be maintained in a high degree of readiness, such as a network connection or modem, which would thus respond to queries at any time of the day or night.

The ultrasound signal path may be set to different inactive state levels from which it can return to full operation in a timeframe desired by the system operator. For instance, processors in the ultrasound signal path can be set to an idle state in which peripheral devices controlled or accessed by the processors including the nonvolatile disk drives servicing the processors are powered down. The processors and their volatile memory (RAM) continue to operate normally so that full operation can be restored almost immediately. In a lower inactive state, in addition to powering down the peripheral devices, the clock rate of the processors is reduced to a lower rate during inactive periods. The processors continue to be energized, as does the volatile memory used by the processors, which enables their resumption to full operability in fractions of a second. In an even lower inactive state the processors themselves are powered down, and the context, or variable data, of the processors such as register values, stacks and index values of the processors are stored in RAM, which remains energized. When power is restored to the processors a pointer restores the context of the processor to its state prior to shutdown, and full operability resumes fairly rapidly. In yet an even lower inactive state, the processor context is stored in RAM, and the RAM data is stored in nonvolatile (disk or semiconductor, e.g., flash) storage. The nonvolatile storage, RAM and processor are then shut down. When operation is resumed the RAM data is retrieved from the nonvolatile storage, the context of the processor restored, and operation resumes from the point at which it was interrupted. In a machine as complex as an ultrasound system, different processors may have different inactive state levels, chosen as a function of the roles played by the various processors and the speed with which the operator wants the system to return to full operation. If the operator wants the system to return to full operation in fractions of a second, for instance, the CPU board OS may set the lowest inactive state for key processors to be that in which processor clock speed is reduced, but the processors and their volatile memory continue to be energized. If a longer time to resume operation is acceptable, a lower inactive state would be used. The sizes of data blocks used by the system is also a consideration. If large blocks of data are needed to configure the beamformer for scanhead operation and the time needed to restore the beamformer data from disk is unacceptable, the OS can cause the RAM memory of the beamformer in which the data is stored to be continuously energized, obviating to restore the data from disk.

Figure 1A:
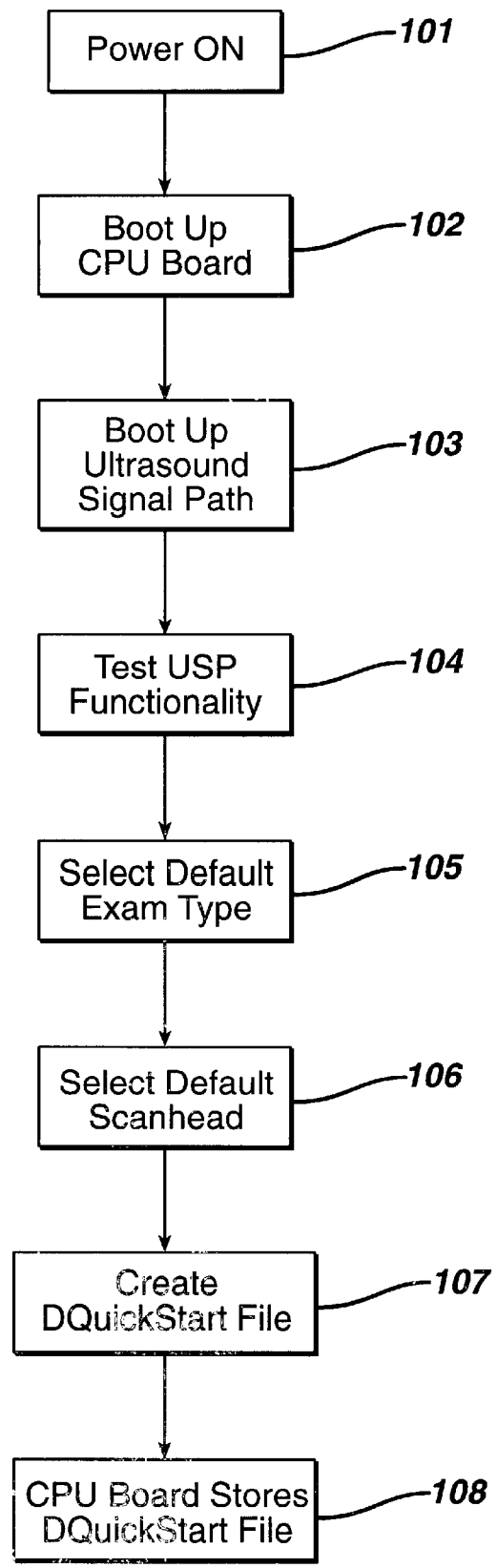

The following drawings illustrate flowcharts for operating an ultrasound system in accordance with some of the foregoing considerations and options. These embodiments describe implementations of the present invention by an OS for ease of illustration; however, it will be appreciated that in a constructed embodiment the invention may be implemented in whole or in part by the OS, application software, BIOS software, or a combination thereof. The present invention can also be implemented in hardware such as by FPGA (field programmable gate array) control in lieu of OS control. As used herein the term OS refers to any of these approaches. FIG. 1a illustrates the flowchart of a process for initializing a default operating state for the ultrasound system. The default operating state is typically one which an operator uses most often. If the ultrasound system operator is an obstetrician, for instance, the default operating state may be an obstetrical exam with a particular curved array scanhead. If the ultrasound system operator is a cardiologist, the default operating state may be a cardiac echo exam with a particular phased array scanhead. The default operating state would typically be initialized the first time the operator uses the ultrasound system, although it can be set or altered at a later point in time. In the process illustrated in FIG. 1a, the ultrasound system is turned on (101) and the CPU board and its OS boot up (102). The OS in turn causes the ultrasound signal path to boot up (103). When the ultrasound signal path is fully operational its functionality is tested (104) to verify that the system is fully functional, a step which may be selectively bypassed by the operator. The operator then uses the user interface to select the default exam type (105). If the operator is an obstetrician, for example, an obstetrical exam may be selected. The operator also selects the scanhead to be used for the preferred exam (106). When all of the necessary parameters of the default operating state have been selected by the operator, the ultrasound system, preferably the OS, creates a file which defines the default operating state, referred to herein as the "DQuickStart" file (107). The OS then stores the DQuickStart file at a storage location from which it can be retrieved when needed, preferably on nonvolatile storage media such as disk storage 34. When the ultrasound system is restarted under several of the conditions discussed below, the OS retrieves the DQuickStart file and initializes the ultrasound system for operation in the predetermined default operating state.

Figure 2A:
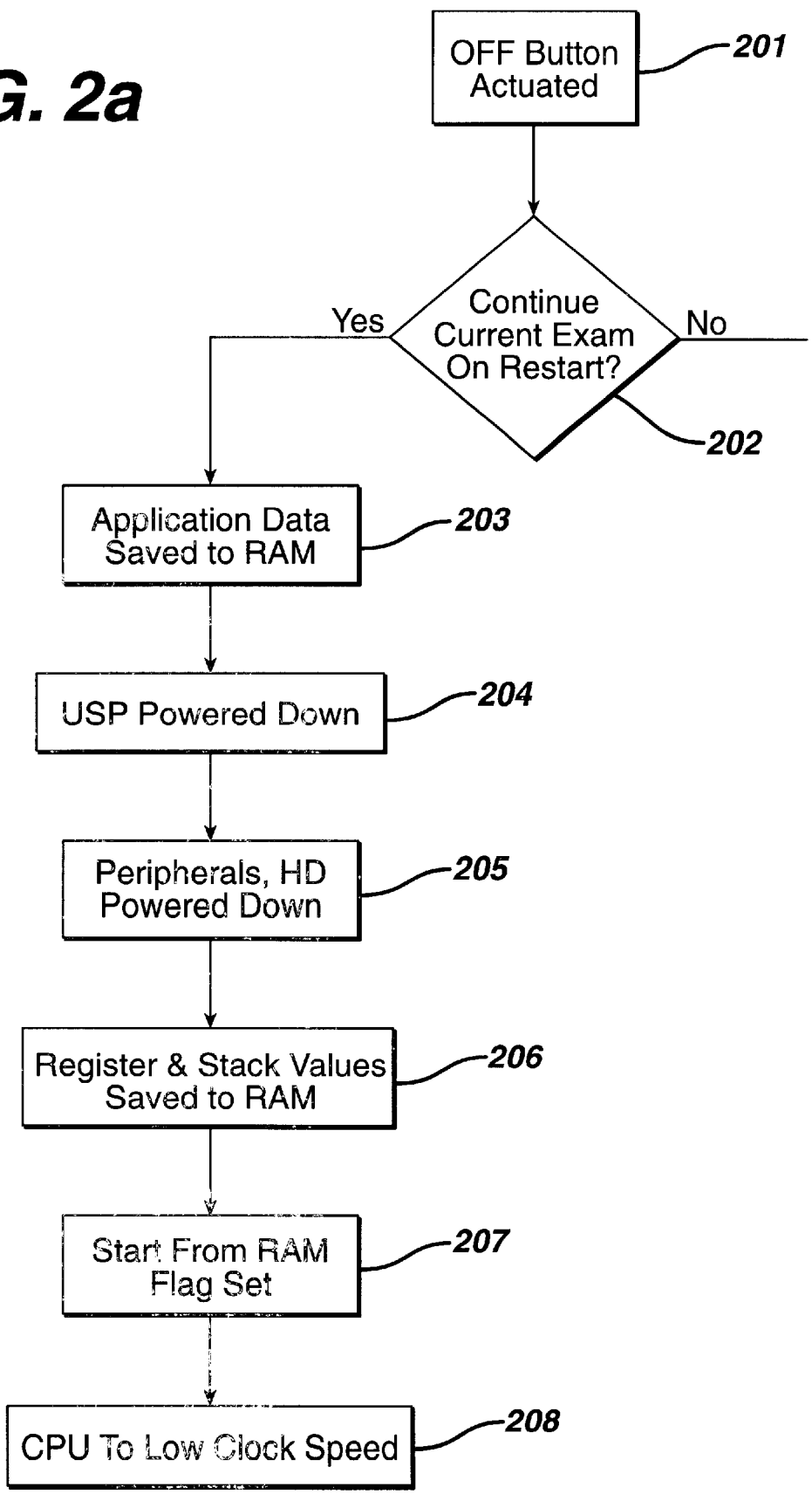

When a conventional ultrasound system is turned off, it proceeds through a lengthy process of terminating operations and shutting down modules and processors. When the power-down process is completed, generally the only circuit which is active is the battery-supported chip which maintains the system clock and calendar. All other circuitry is completely turned off. FIG. 2a illustrates a power-down state of the present invention from which full operability of the ultrasound system may be resumed fairly rapidly. Unlike the conventional power-down sequence, key system circuits continue to be energized. In FIG. 2a the OFF button is actuated (201) and the ultrasound system queries the operator as to whether the current ultrasound exam is to be continued when the system is restarted (202). In this example the operator responds that the current examination is to be continued. The application data for the current exam is saved to RAM (203) and the OS powers down the ultrasound signal path (204). The OS also powers down the ultrasound system's peripheral devices or puts them in a suspend state, including the hard drive (HD) disk storage 34 (205). The register and stack values (context) of the CPU are saved to RAM (206) and a flag is set instructing the CPU to use the saved values when it is restarted (207). The CPU is then clocked at a low clock speed (208) to conserve energy.

Figure 3A:
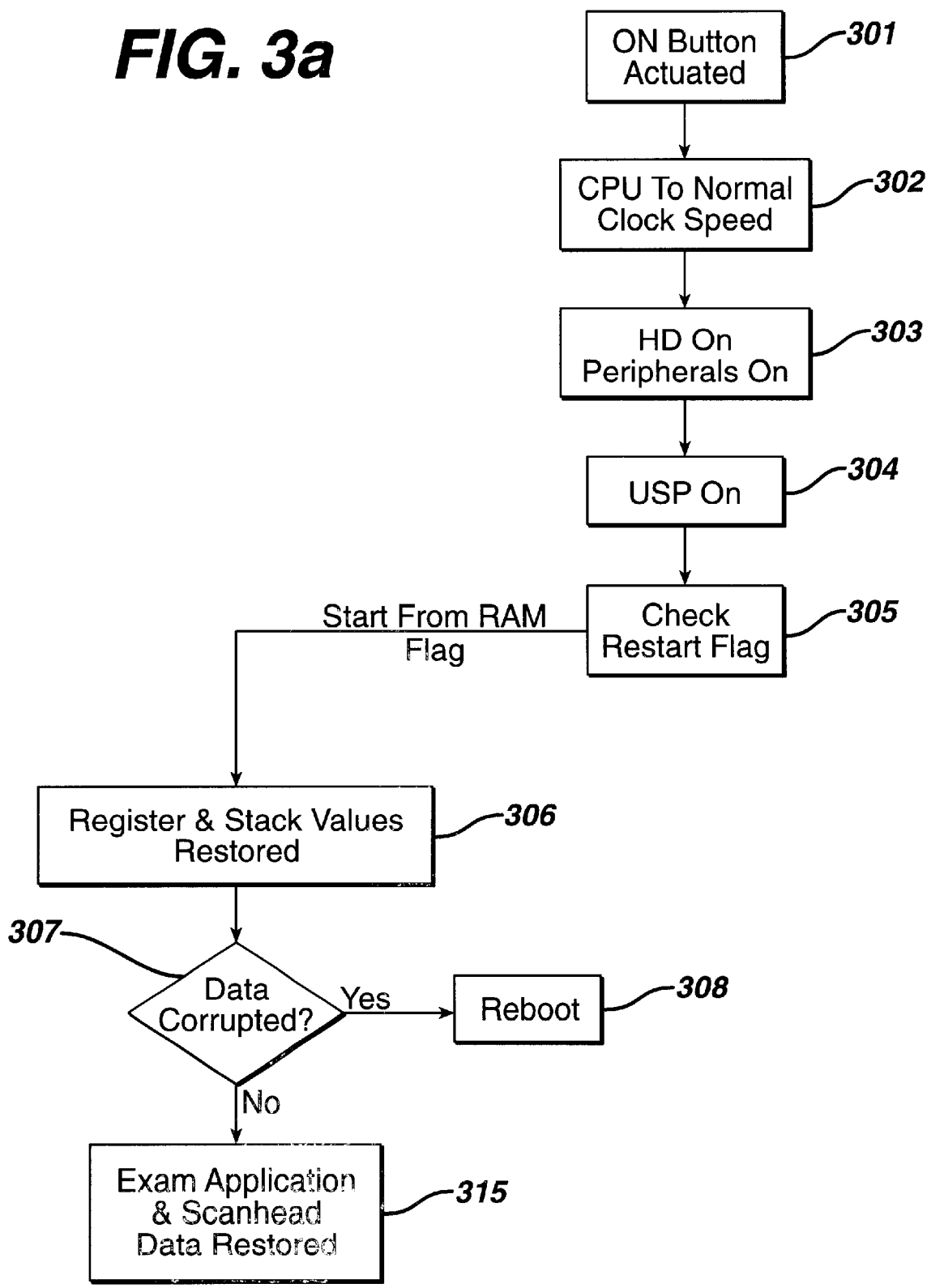

The ultrasound system may be restarted from this state by following the process charted in FIG. 3a. When the ultrasound system ON button is actuated (301) the CPU is clocked at its normal clock rate (302). The peripheral devices including the hard drive are turned on (303) and power is restored to the ultrasound signal path (304). The OS checks the restart flag (305) and finds that it is set to restart from RAM. The register and stack values of the CPU are restored from RAM (306) and checked for corrupted data (307). Since the ultrasound system may have been left in its inactive state for a considerable period of time, such as overnight or for several days or longer, it is prudent to check for data corruption since the ultrasound system is being relied upon to provide patient diagnostic information. If corrupted data is found, a full recovery bootup is performed (308). If no data corruption is found the data previously stored for the examination, the application data, and the scanhead data are restored to the ultrasound signal path (315). The system is now ready to continue the same exam that was underway when it was turned off.

In this and the other quick start sequences described below, it is seen that the step (104) of testing full functionality of the ultrasound signal path is not performed during the rapid restoration of system operability. That is because such self-testing can be very time-consuming, detracting from the desired quick system restart. However, such functionality testing should be performed to continually assure accurate system functionality. In an embodiment of the present invention such functionality testing is performed at run-time, either as part of mode transitions, in the background, or when periodic idle or partially inactive states are encountered such as when an image is frozen on the screen. Uninterrupted full functionality testing of the ultrasound signal path is performed automatically on a cold start reboot. At other times such functionality testing is intermittently conducted by the OS when such scheduling can be conducted without interruption of operations commanded by the operator, such as during the night when the system is not in use. Thus, safety hazards and risk concerns are abated on a periodic but continual basis.

Variations of these processes are possible. Instead of powering down the entire ultrasound signal path (204) the OS may leave some or all of the processors of the ultrasound signal path in one or more idle states or low clock speeds, or turn off some of the components and modules of the ultrasound signal path processors while leaving others energized. For instance, the volatile memory holding data for the beamformer may be left in an energized condition. The OS can do this by commanding the signal path power supply 18 by way of the control module 15 and the command line 17 to switch power off to all elements of the ultrasound signal path except the beamformer RAM. As another alternative, rather than switching the CPU to a low clock speed, the OS may issue a command to the CPU power supply 32 over command line 36 to switch power off to all CPU board components except the board's RAM. While this action would increase the time required by the system to return to full operability, it would enable the CPU power supply to operate at an output level of approximately 5 watts or less, which may be sustained by battery power for an appreciable amount of time.

Figure 2B:
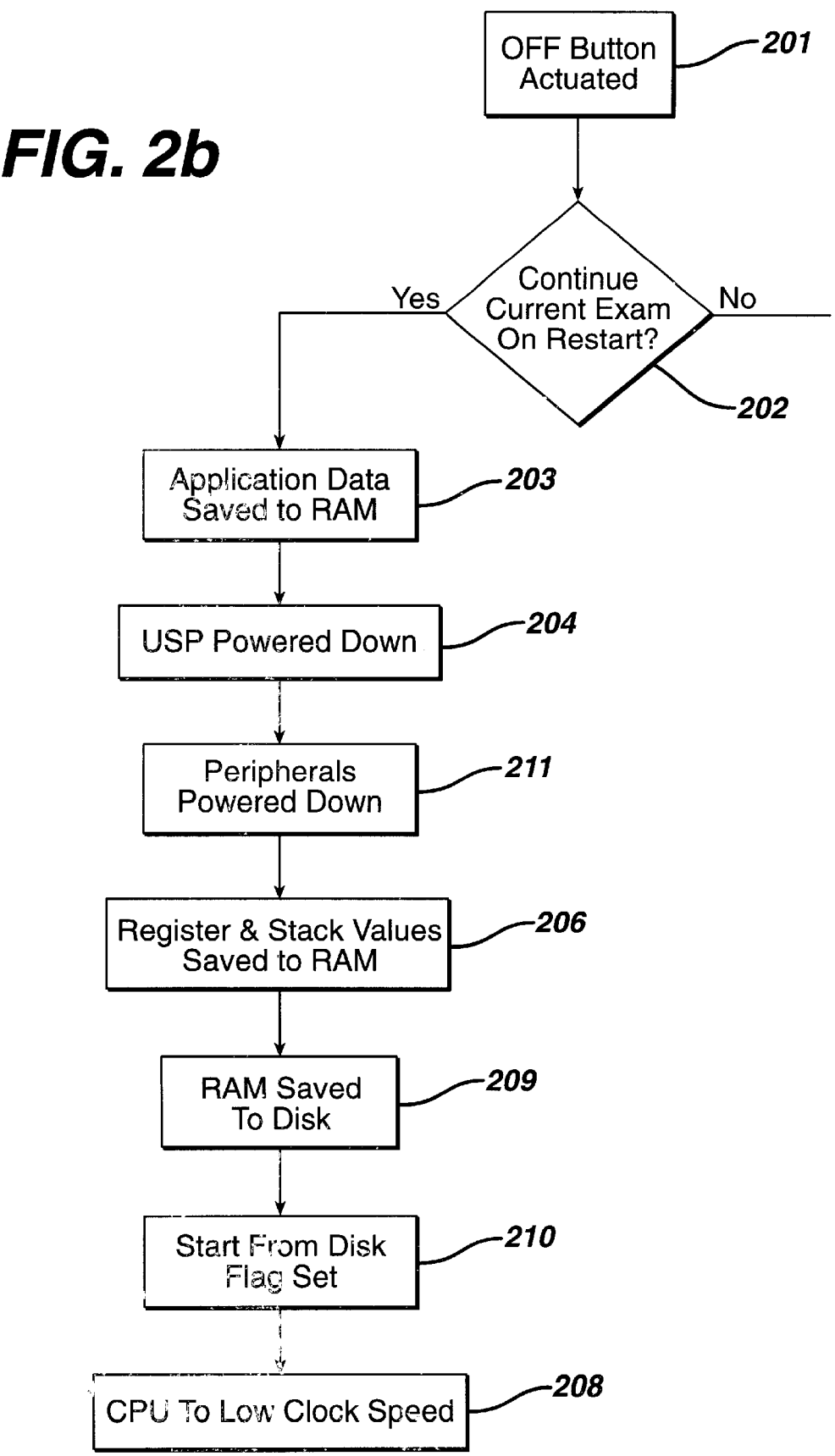

FIG. 2b illustrates a procedure by which the ultrasound system is "turned off" to a lower state of readiness, requiring more time to be restored to full operability but exhibiting lower power consumption when "turned off." After the operator actuates the OFF button (201) and elects to continue the current examination when the system is restarted (202), the application data for the current exam is save to RAM (203), the ultrasound signal path is powered down (204), the peripheral devices are powered down (211), and the register and stack values of the CPU are saved to RAM (206). The data stored in RAM is saved to nonvolatile disk or semiconductor storage (209) and a flag is set to notify the CPU to start from the data in nonvolatile storage when operation is resumed. The disk drive and RAM is powered down and the CPU is switched to a low clock speed. Alternatively, the CPU may also be powered down as the data needed on restart is retained in nonvolatile storage. This will require the CPU to reboot on restart, but will not require power to be maintained to the CPU while the system is off.

Figure 3B:
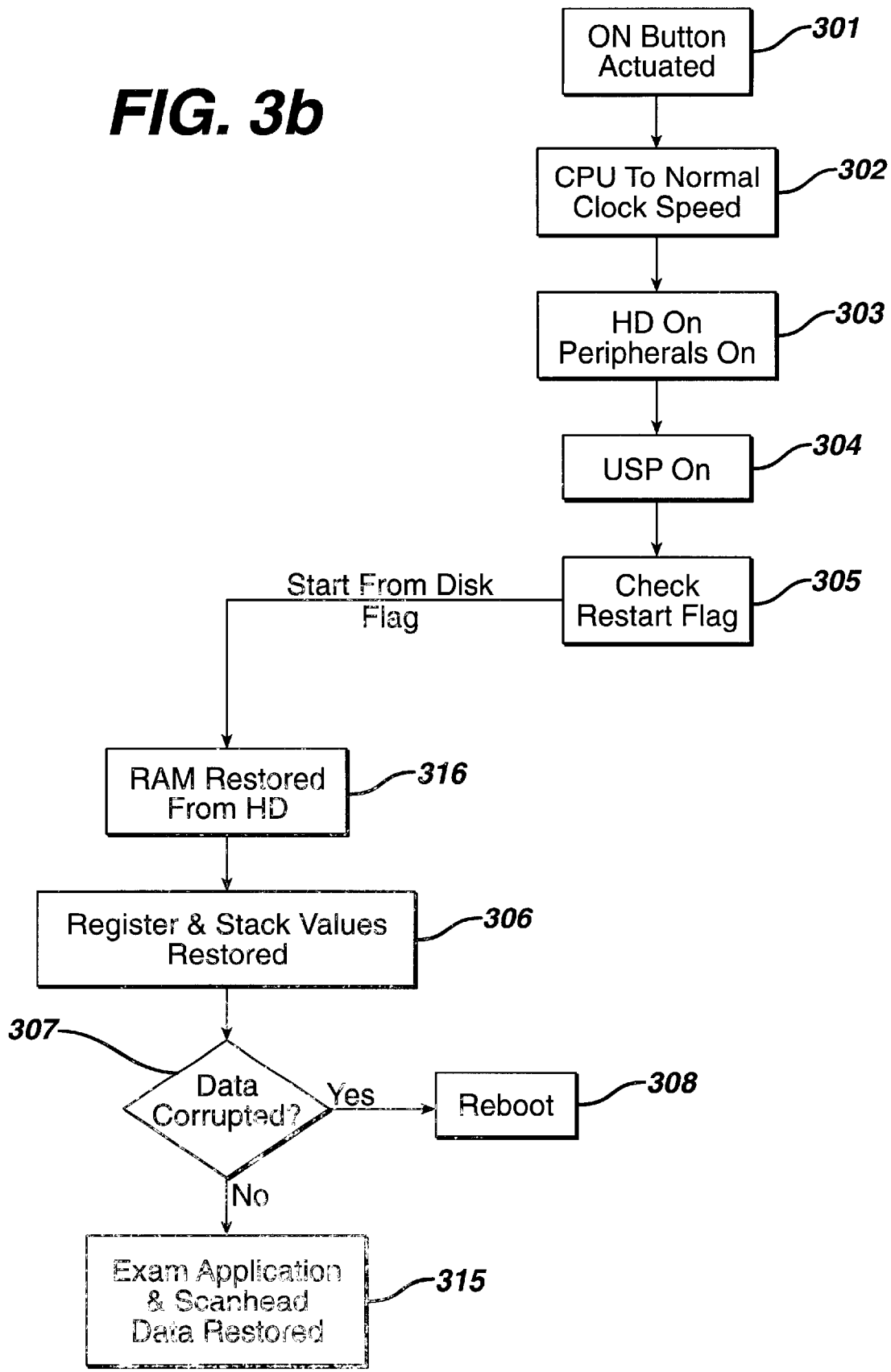

The ultrasound system may be restarted from this off state by following the sequence shown in FIG. 3b. When the ON button is actuated (301) the process follows the same procedure diagrammed in FIG. 3a up to the point where the restart flag is checked (305). Here the OS sees that the "Start From Disk" flag has been set, and consequently the data stored on the hard drive is restored to RAM (316). The register and stack values of the CPU are restored (306), and a data corruption check is performed (307). If no data corruption is found the examination application data and the scanhead data are restored (315), and the system is once again ready to continue the previous exam. As before, variations are possible such as leaving portions of the ultrasound signal path energized and/or operating at selected idle levels to enable a quicker restart.

Figure 2C:
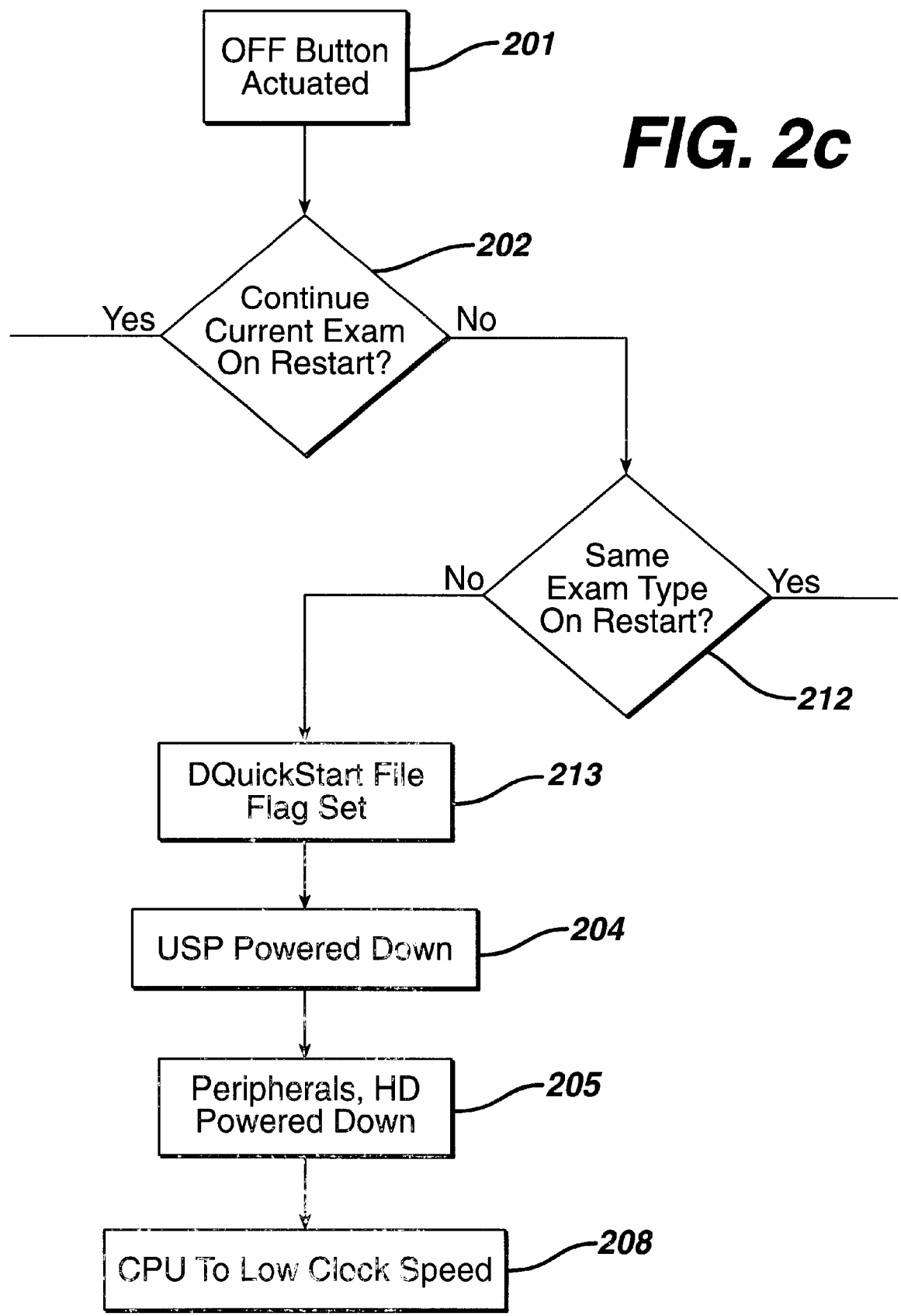

In the previous scenarios the operator has elected to have the system continue the current ultrasound exam when the ultrasound system is restarted. FIG. 2c shows one possible scenario when the operator has elected not to continue the same exam on restart. When the operator makes this election (202, the system queries whether the same type of examination as the most recent one is to be used on restart (212). If the operator routinely uses the ultrasound system for a particular type of cardiac exam, for instance, the choice might be made to restart the system for the same type of cardiac exam as that which has just been completed. But if the operator wants a different exam the next time the system is used or is not sure what type of exam will be performed next by the system, the operator answers "No", as shown in the drawing. The OS responds by setting a flag for the DQuickStart file (213), powering down the ultrasound signal path (204), powering down the peripherals including the hard drive (205), and setting the CPU to a low clock speed (208). When the system is restarted the ultrasound system follows the sequence shown in FIG. 3c. When the ON button is actuated (301) the CPU is returned to its normal clock speed (302) and the hard drive and peripheral devices are turned on (303). The ultrasound signal path is turned on (304) and the OS checks the restart flag (305). Upon finding the DQuickStart flag set, the DQuickStart file is selected from nonvolatile storage (309) and the previously set default operating parameters are implemented. The ultrasound signal path is conditioned for starting the default exam application (310) and the beamformer is set up to operate the default scanhead (311) or, if it is unavailable, a scanhead presently connected to the ultrasound system. The ultrasound system is now ready to perform the default exam.

As in the previous examples, variations of this scenario may be employed. Instead of switching the CPU to a low clock speed, the CPU board can be turned off, as the DQuickStart file is stored in nonvolatile storage; only the restart flag needs to be maintained. This would take more time to restart, as the CPU board would have to be rebooted. As another alternative which would result in an even faster restart, instead of setting the DQuickStart flag during the power-down sequence, the parameters of the DQuickStart file could be loaded into RAM and power to the RAM maintained so that the OS could immediately implement the DQuickStart application without having to recall the DQuickStart file from storage upon restart.

Figure 3C:
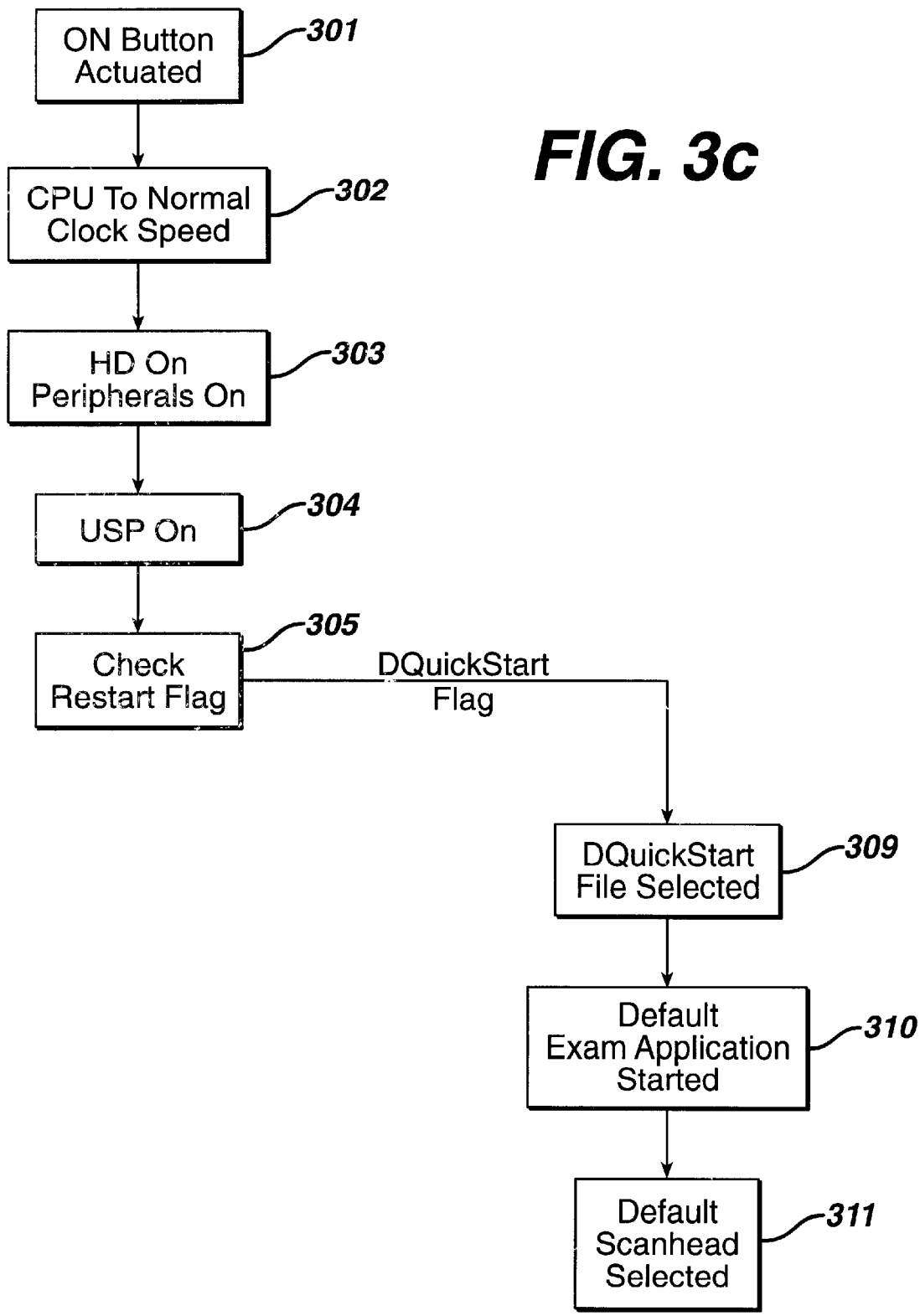

FIG. 2d shows a sequence of events that occur when the operator elects to begin the same type of exam as that which was just completed when the ultrasound system is restarted. When the operator makes this election (212), the OS builds a file called CQuickStart, which contains parameters of the type of exam just completed, including the scanhead used (214). The CQuickStart file is saved to disk (or, in one of the alternatives described above, is stored in RAM), and a flag is set for the CQuickStart file (215). The ultrasound signal path is powered down (204), the peripherals and hard drive powered down (205), and the CPU is set to a low clock speed (208). When the ultrasound system is turned on (301)

as illustrated in FIG. 3d, the normal CPU clock speed is resumed (302), the hard drive and peripherals turned on (303), and the ultrasound signal path is turned on (304). The OS checks the restart flag and finds that the CQuickStart flag is set (305). The OS retrieves the CQuickStart file from disk (or implements it immediately if it was stored in RAM) (312), and starts the exam application identified by the CQuickStart file (313), including setting up the beamformer for the scanhead identified by the file (314). The alternatives applicable to the previous scenario of FIGS. 2c and 3c are also applicable to this one.

Figure 4:
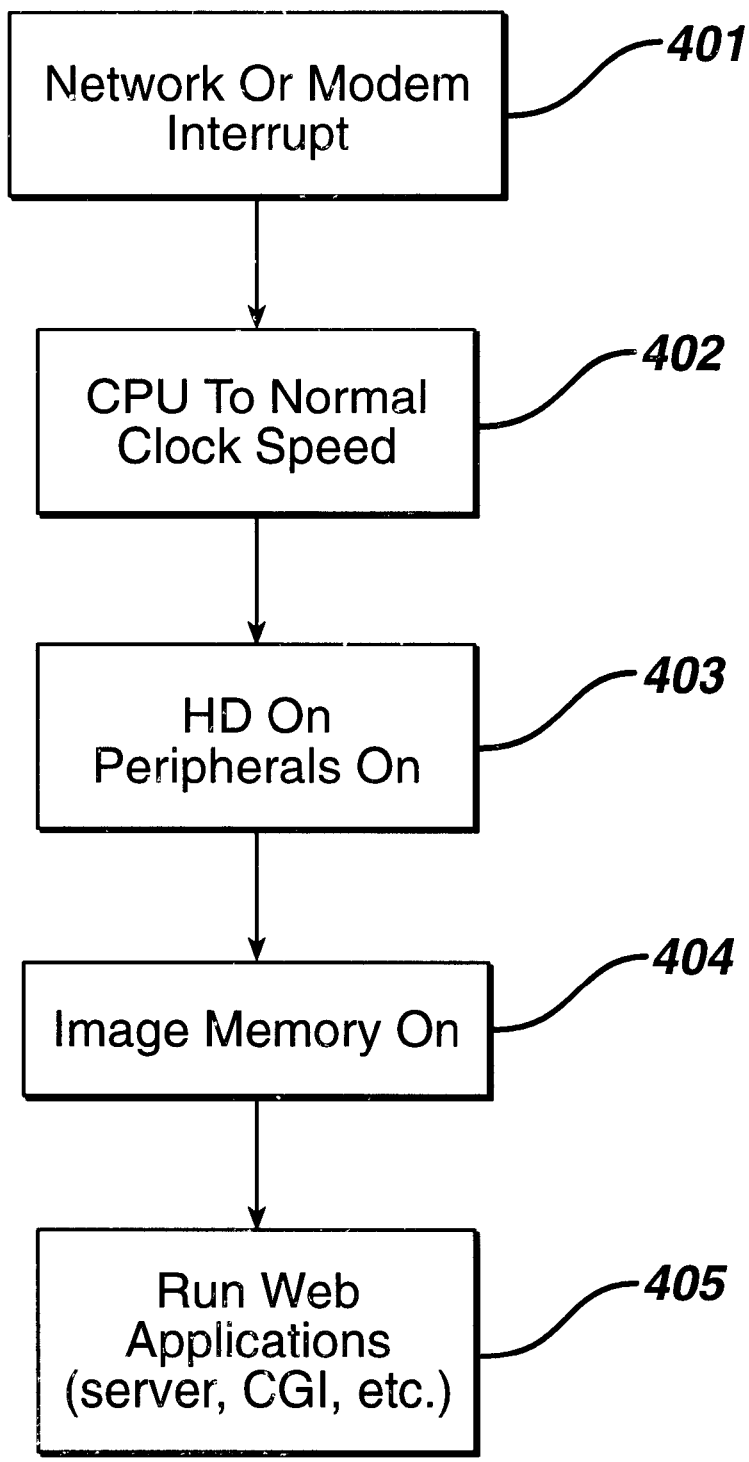
FIG. 4 illustrates a method by which an inactive ultrasound system can respond to a remote inquiry.

As mentioned above, when the OS powers down different elements of the ultrasound system it will power them to an idle level which allows them to be returned to full operability in the timeframe required-by the user. Different elements of the ultrasound system may be set to different idle levels, and these levels may vary for different users as different users may have different demands for the time in which the ultrasound system must restart. The OS will also power down different elements of the system in consideration of the type of functions they perform, as previously illustrated by the example of maintaining power to the beamformer memory. FIG. 4 illustrates another example of this. An ultrasound system which is externally accessible over a network or modem may need to be available for remote querying at any time. For example, remote diagnostics may be performed at night when the ultrasound system is not otherwise in use, as described for instance in U.S. patent application Ser. No. 09/534,143, filed Mar. 23, 2000. As another example, the diagnosing physician may want to review images stored on the ultrasound system from his home after the ultrasound lab has closed for the day. Such a scenario is described in U.S. Pat. No. 5,851,186. In these cases, the ultrasound system is essentially "on call" 24 hours a day. In this mode, when the ultrasound system is turned off at the end of the day, the network interface or modem may be in a suspend or power-down state, but still aware of network or phone activity such that it can be fully active if called. The CPU can be put in a low power state, or even turned off, so long as it continues to be responsive to an interrupt from the network or modem to handle external queries. The CPU itself can be responsive to such an interrupt in an idle (e.g., low clock speed) state, or the chipset on the CPU board can be responsive to such an interrupt and restart the CPU accordingly. In some cases the BIOS software on the CPU board can be programmed to handle these interrupts.

As an example, a physician desires to use his home computer to view an image acquired the previous business day by the ultrasound system. The physician connects to the ultrasound system either through the network connection or modem as shown in FIG. 4, which sends an interrupt to the CPU board (401). In the case where the CPU was powered down to a low clock speed, the CPU responds to the interrupt by resuming its normal clock speed (402). In the case where the CPU was turned off, the CPU board chipset responds to the interrupt by restarting the CPU. The hard drive and other peripherals may be turned on (403) if needed to respond to the request, as they may be required to run Web applications to respond to an Internet browser. The OS turns on the memory device where the ultrasound images are stored (404). In the example of FIG. 1 the ultrasound images are stored on an image store 22 connected to the ultrasound signal path and the CPU board. The OS then runs the communications software needed to respond to the request, such as Web applications software (405). As described in the aforementioned patent, a Web server can transmit an image file index to the physician who selects the image desired. The desired image is then retrieved from the image memory or disk and transmitted over the network, modem, or Internet to the physician, who then views it on the screen of his home computer. After the communication has ended, the hard drive, image memory, peripherals and CPU can be powered down again to await the next query in a low power state.

Figure 5:
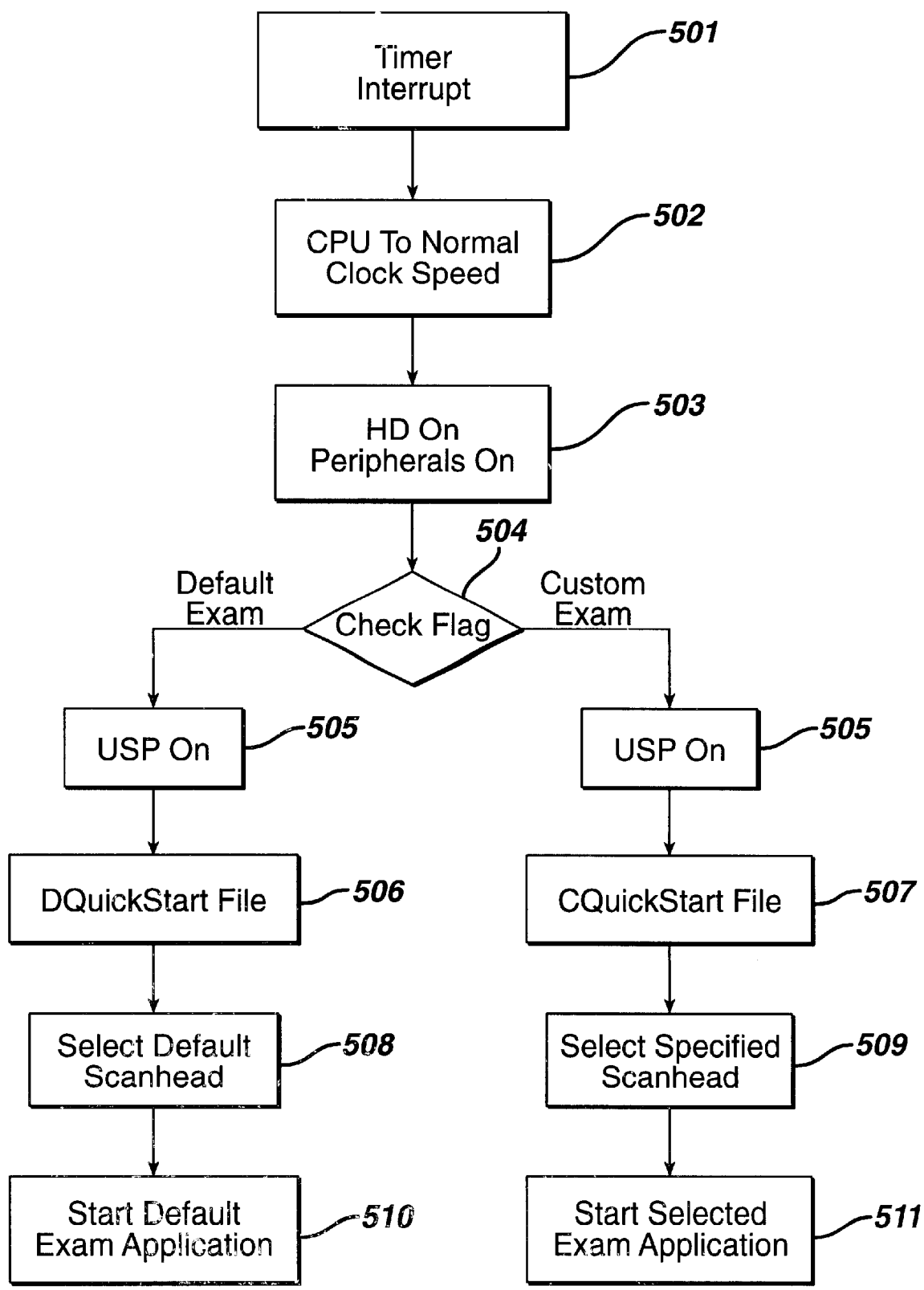
FIG. 5 illustrates a method by which an inactive ultrasound system automatically prepares for scanning at a predetermined time.

With the ultrasound system having the ability to power up and power down the system selectively, a procedure such as that shown in FIG. 5 can be employed to automatically restart the ultrasound system at a predetermined time. This allows the ultrasound system to be shut down when it is not used overnight, but to be ready for scanning when the ultrasound lab is opened the next day. At the time the ultrasound system is turned off, the operator enters a command for the ultrasound system to restart at a designated time and date. If the ultrasound lab opens at 8 a.m. the next day, it may be desirable to have the ultrasound system turn on at 7:45 a.m. and to perform a self-diagnosis at the time so that the system is fully ready for scanning at 8 a.m. When the operator turns the ultrasound system off, the selection is made to restart the system for the default exam or a custom exam (including the most recently performed exam as explained above), and the appropriate QuickStart file is flagged. The system is then shut down to the desired idle level; in this example, the CPU is switched to a low clock speed. A timer in the ultrasound system, which may be implemented on the CPU board, keeps track of the time and when the appointed start time occurs the timer sends an interrupt to the CPU board (501). In response to the interrupt the CPU returns to the normal clock speed (502), and the OS turns on the hard drive and peripherals (503). The OS then checks to see whether the a flag is set for the default exam or a custom exam (504). If the default exam has been flagged, the ultrasound signal path is turned on (505) and the DQuickStart file is retrieved. The beamformer is programmed for the scanhead used in the default examination (508) and the default exam application is set up on the ultrasound system (510). A full self-test of system functionality may be performed. The ultrasound system is then fully ready for scanning when the operator arrives to use it.

When the OS finds that the custom exam flag has been set, the ultrasound signal path is turned on (505) and the CQuickStart file is retrieved (507) which contains the parameters of the exam which the operator wants to perform first. The beamformer is programmed for the scanhead of the custom exam (509) and the custom exam application is set up on the ultrasound system (511). A full self-test of system functionality may be performed. Thus, the ultrasound system is ready to use immediately when the ultrasound lab is opened in the morning without having to leave the system fully powered up overnight.

As discussed above, a high performance ultrasound system can consume approximately 1000 watts of power, even when sitting unused. This power consumption will produce a heating effect which must be dissipated by the lab or hospital's air conditioning system, which costs money. Furthermore, the heating of components in the system can reduce component life, leading to degraded system reliability. FIG. 6 illustrates an approach to reducing this cost and unnecessary component heat dissipation, which is for the ultrasound system to progressively turn off its modules and subsystems when it is sitting unused for a period of time. In a preferred implementation the user is given the opportunity to activate or deactivate such a progressive shutdown, select the time which passes before the progressive shutdown commences, and select the time passages between the successive steps of the shutdown. The order in which the various components of the system shut down can also be changed. In the progressive sequence of FIG. 6 the first element to be shut down is the display device, which may first be put on standby (601) and, after a further passage of time, completely powered down. After further time the OS powers down the ultrasound system peripheral devices such as printers and recorders (602). After further time, any unsaved exam data and the register and stack values of the CPU (context) are stored to RAM (603) and the RAM data saved to disk (604). The ultrasound signal path is powered down (605) and the CPU board's peripherals and hard drive are powered down (606). Finally the CPU is set to an idle state, in this example a low clock speed (607). The ultrasound system is now consuming only a small amount of power, perhaps 5 watts or less, but the CPU, still being energized, can restart the ultrasound system in a relatively short amount of time.

In a variation of the sequence of FIG. 6, the OS is continually monitoring the use of the ultrasound system and turning modules and components off and on where the situation permits to effect a lower overall power consumption and component heating. Modules and subsystems may be placed into low power states for seconds and even fractions of seconds where possible to achieve this. For example, the operator may interrupt real time imaging to freeze an image on the display screen. Sensing this state, the OS can maintain power to the display 16, the image store 22 where the frozen image is stored, and that portion of the ultrasound signal path which applies image display signals to the display such as the video driver of the system. The transmit and receive beamformers can be set to an inactive, low power state at this time, as can the signal and image processing portions of the ultrasound signal path 14, since real time imaging has been suspended. To the operator, this suspense state is transparent, as the frozen image is maintained on the display as the operator has commanded. This reduces the power consumption and heating of those subsystems of the ultrasound signal path 14 which have been placed in the low power state. The 1200 watt consumption of an ultrasound signal path can be momentarily reduced to 200 watts, for example. When the operator unfreezes the image to resume real time imaging, the low power subsystems are restored to full operability immediately, without any interruption in system operability apparent to the operator. Over time, such periodic reductions in power consumption can reduce the heating and hence prolong the life of components of the ultrasound signal path, as well as reduce the air conditioning load imposed by the ultrasound system.

While such periodic reductions in system power consumption will reduce thermal emission by the ultrasound system, this capability may also be used to reduce audible emission as well. The noise made by an operating ultrasound system is the humming of fans used to cool the electronic components and power supplies. When the overall power consumption of the ultrasound system and component heating are reduced, the need for fan cooling is reduced as well. When individual components, modules, or subsystems are powered down or turned off even for short intervals, the fans used to cool them can be operated at a reduced fan speed or even periodically turned off. Thus, thermal levels in the ultrasound system can be monitored by the CPU board OS and the speed of the cooling fans adjusted when possible. It may be appreciated that during a 30 minute ultrasound exam, the system operator may spend half the time changing operating states, making measurements on frozen images, talking to the patient, and other non-real-time scanning activities. Advantage can be taken of these circumstances by the OS to control the ultrasound system so that it is fully operational only when required. This can lead to a reduction in thermal and noise pollution by an equivalent amount.

The embodiment of FIG. 1 is seen to include a battery backup, an interim power source which can sustain key elements of the ultrasound system for periods when a.c. power is not available. This ability to sustain key elements such as the CPU and RAM even when the system is not plugged in to its a.c. power source enables the ultrasound system to be moved and restarted very quickly to meet the needs of a modern hospital. As explained at the outset of this patent, it is often necessary to quickly move an ultrasound system from one area of a hospital to another to perform a diagnosis in another department of the hospital as soon as possible. But this cannot be done when an ultrasound system has to sequence through a lengthy shutdown procedure before it can be turned off and unplugged, and must go through a lengthy boot-up sequence when restarted at the new location. The ultrasound system shown in FIG. 1 by use of the processes shown in the preceding flowcharts can be quickly moved without these delays. For example suppose that the ultrasound system is called to be moved from the ultrasound lab to the delivery room in obstetrics for an immediate scan. The operator can touch the OFF button, pull the ultrasound system plug 40 from the wall, and begin to move the ultrasound system to the obstetrics ward without waiting for any of the shutdown procedure to occur. When the plug is pulled the ultrasound system switches to its backup battery power source, and as it is being moved the ultrasound system will shut itself down using one of the sequences described above. The ultrasound system can shut itself down for a restart to the default exam (which may in this example be an obstetrical exam) or to the most recently used exam for instance. Preferably the ultrasound system under these conditions will not shut the CPU down completely, but will leave the CPU and its RAM energized so that the system can be restarted quickly when it arrives at the obstetrics ward for the emergency exam. If desired, the OS can be programmed to respond to a loss of a.c. power during a shutdown sequence by powering down to a high state of readiness from which it can be returned to full operability almost instantly. For example, by sensing the loss of a.c. power, or sensing the switchover to battery power, or detecting the lack of operator responses to the queries posed during shutdown (e.g., restart the same exam?) the OS would continue to maintain power to all processors and volatile storage devices (RAM) in the ultrasound system for as long as sufficient battery power was available to do so. As another example the ultrasound system may experience an inadvertent loss of a.c. power, for instance, if the a.c. power cord is accidentally pulled from the wall or the circuit breaker for the a.c. line powering the system trips. In such instances the OS automatically performs a shutdown such that the current exam is resumed on restart (FIGS. 2*a* and 3*a*). Alternatively, if battery capacity is sufficient, the ultrasound system can be powered in a fully active state by the battery until the battery is substantially discharged, at which point a shutdown is automatically performed. Devices which consume relatively large amounts of energy and do not retain critical data in volatile storage, such as the display and the scanhead's transducer drivers, could be shut down to conserve battery power while still affording the ability to restart almost instantly. When the ultrasound system arrives in the obstetrics ward in the first example, is plugged in, and the ON button depressed, it is ready for scanning virtually immediately.

In an embodiment where the ultrasound system does not contain battery backup power, some of the aforementioned delays can still be avoided. For instance, sufficiently sized capacitors in the power supply system can retain sufficient energy to sustain an OS shutdown sequence even in the absence of battery backup. Such capacitively stored energy could power the CPU board for the time required to complete an orderly shutdown. The operator could thus press the OFF button, pull the a.c. plug from the wall and begin to move the ultrasound system. The capacitive source would provide power for shutdown during this time. When the CPU board senses that a.c. power has been lost prior to completion of a normal shutdown, the OS can immediately cut power from nonessential or high power consuming devices such as the display, transducer drivers, printers and recorders. The capacitively stored power would then be sustainable to shut down data components and processors in a rapid but orderly manner. This shutdown sequence would end with the complete shutdown of all components in the ultrasound system, including the CPU and RAM on the CPU board.

What is claimed is:

1. An ultrasound system, including components exhibiting different states of operability, which reduces system power consumption comprising:

a processor; and control software running on said processor which acts to reduce the power consumption of the ultrasound system by changing the states of operability of components of the ultrasound system, wherein the memory comprises a volatile memory; and further comprising a nonvolatile memory coupled to the processor; and wherein the control software acts to store data of the volatile memory in the nonvolatile memory and turns off the memories and processor.

2. An ultrasound system, including components exhibiting different states of operability, which reduces system power consumption comprising:

a processor; and control software running on said processor which acts to reduce the power consumption of the ultrasound system by changing the states of operability of components of the ultrasound system, wherein the components include a processor and a memory coupled to the processor; and wherein the control software acts to turn off the processor while maintaining power to the memory.

3. An ultrasound system, including components exhibiting different states of operability, which reduces system power consumption comprising:

a processor which is operable at different clock speeds; and control software running on said processor which acts to reduce the power consumption of the ultrasound system by changing the states of operability of components of the ultrasound system, wherein the components include a processor and a memory coupled to the processor; and wherein the control software acts to reduce the clock speed of the processor while maintaining power to the memory.

* * * * *